United States Patent
Pandey et al.

(10) Patent No.: US 10,641,893 B2
(45) Date of Patent: **\*May 5, 2020**

(54) SYSTEM AND METHOD FOR PHASED ARRAY MATERIAL IMAGING

(71) Applicant: NOBLE SENSORS, LLC, New York, NY (US)

(72) Inventors: Gaurav Pandey, Jersey City, NJ (US); Martin J. Weinberg, New Canaan, CT (US); Richard S. Koplin, New York, NY (US)

(73) Assignee: NOBLE SENSORS, LLC, New York, NY (US)

( * ) Notice: Subject to any disclaimer, the term of this patent is extended or adjusted under 35 U.S.C. 154(b) by 337 days.

This patent is subject to a terminal disclaimer.

(21) Appl. No.: 15/839,297

(22) Filed: Dec. 12, 2017

(65) Prior Publication Data

US 2018/0100923 A1 Apr. 12, 2018

Related U.S. Application Data

(63) Continuation of application No. 15/061,116, filed on Mar. 4, 2016, now Pat. No. 9,841,502.

(Continued)

(51) Int. Cl.
*A61B 8/00* (2006.01)
*G01S 15/89* (2006.01)
(Continued)

(52) U.S. Cl.
CPC .......... *G01S 15/8925* (2013.01); *G01N 29/00* (2013.01); *G01N 29/0654* (2013.01);
(Continued)

(58) Field of Classification Search
CPC ............ G01N 2291/044; G01N 29/00; G01N 29/0654; G01N 29/262; G01S 15/89;
(Continued)

(56) References Cited

U.S. PATENT DOCUMENTS 5,203,335 A 4/1993 Noujaim et al.
5,663,720 A * 9/1997 Weissman ............... G01S 13/91
340/905

(Continued)

FOREIGN PATENT DOCUMENTS

DE 19527779 A1 7/1994

OTHER PUBLICATIONS

An extended European Search Report issued by the European Patent Office dated Nov. 22, 2018 in connection with European patent application No. 16762205.9.

(Continued)

*Primary Examiner* — Timothy A Brainard
(74) *Attorney, Agent, or Firm* — Baker & McKenzie (57) ABSTRACT

A probe is described for analyzing a target using an array of transceivers formed of transmitter/receiver pairs. As opposed to the prior art, the high voltage trigger signals from used to trigger the transmitters are separated from the output signals of the receivers thereby resulting in a simpler and more efficient circuitry. Moreover, the output signals are delayed to compensate for the delays in the echo signals from the target due to the varying distance between the different transceivers and the target. The probe can be used for analyzing pathological organs, as well as many other objects such as gas pipes, airplane wings, etc.

19 Claims, 9 Drawing Sheets

Related U.S. Application Data (60) Provisional application No. 62/129,344, filed on Mar. 6, 2015.

(51) Int. Cl.
*G01N 29/00* (2006.01)
*G01S 7/52* (2006.01)
*G10K 11/34* (2006.01)
*G01N 29/06* (2006.01)
*G01N 29/26* (2006.01)

(52) U.S. Cl.
CPC .......... *G01N 29/262* (2013.01); *G01S 7/5202* (2013.01); *G01S 15/89* (2013.01); *G01S 15/8913* (2013.01); *G01S 15/8915* (2013.01); *G10K 11/346* (2013.01); *A61B 8/4488* (2013.01); *G01N 2291/044* (2013.01)

(58) Field of Classification Search
CPC ............ G01S 15/8913; G01S 15/8915; G01S 15/8925; G01S 7/5202; G10K 11/34
USPC ......................................................... 342/90
See application file for complete search history.

(56) References Cited

U.S. PATENT DOCUMENTS

| | | | |
|---|---|---|---|
| 5,675,554 A | | 10/1997 | Cole et al. |
| 6,142,946 A | | 11/2000 | Hwang et al. |
| 9,841,502 B2 | * | 12/2017 | Pandey ................... G01S 15/89 |
| 2002/0045830 A1 | | 4/2002 | Powers et al. |
| 2003/0055337 A1 | * | 3/2003 | Lin ....................... B06B 1/0622 |
| | | | 600/459 |
| 2004/0155810 A1 | | 8/2004 | Witten |
| 2005/0113698 A1 | | 5/2005 | Kristoffersen et al. |
| 2010/0274139 A1 | | 10/2010 | Fukukita et al. |
| 2011/0015523 A1 | * | 1/2011 | Sabata ..................... A61B 8/12 |
| | | | 600/443 |
| 2011/0082374 A1 | * | 4/2011 | Main ................... A61B 5/02007 |
| | | | 600/458 |
| 2011/0122024 A1 | | 5/2011 | Eidloth et al. |
| 2011/0208060 A1 | * | 8/2011 | Haase .................... A61B 5/021 |
| | | | 600/453 |
| 2012/0071760 A1 | * | 3/2012 | Miller ................. G01S 7/52017 |
| | | | 600/443 |
| 2012/0076229 A1 | | 3/2012 | Brobston et al. |
| 2013/0150723 A1 | | 6/2013 | Satoh |
| 2013/0158404 A1 | | 6/2013 | Towfiq et al. |
| 2013/0283918 A1 | | 10/2013 | Habermehl et al. |
| 2015/0016223 A1 | * | 1/2015 | Dickinson ............... G06F 3/043 |
| | | | 367/87 |
| 2015/0071031 A1 | * | 3/2015 | Siedenburg ......... G01S 15/8915 |
| | | | 367/11 |

OTHER PUBLICATIONS

J. Fessler: "Chapter a Ultrasound Arrays", Sep. 30, 2009 (Sep. 30, 2009), Retrieved from the Internet: URL:https://web.eecs.umich.edu/~fessler/course/516/I/ca-array-1-8.pdf [retrieved on Nov. 14, 2018].

Wygant I et al: "An integrated circuit with transmit beamforming flip-chip bonded to a 2-D CMUT array for 3-D ultrasound imaging", IEEE UFFC, US, vol. 56, No. 10, Oct. 1, 2009 (Oct. 1, 2009), pp. 2145-2156.

An International Search Report (ISR) mailed by the USPTO in its capacity as the International Searching Authority dated May 19, 2016 in the counterpart International Application No. PCT/US16/20859.

* cited by examiner

FIG. 1 (PRIOR ART)

(PRIOR ART)

FIG. 2

(PRIOR ART)

Novel phased array probe with alternate transmitter and receiver elements -- a) one dimensional probe b) two-dimensional probe. Pre-amplifiers/low noise amplifiers and cables for transmit and receive signals are not shown for two dimensional probe.

Illustration of novel beamformer architecture using a five element phased array.

FIG. 7A

An illustration of the improvement in resolution using the novel delayed trigger technique. A) Reflected echoes resulting from transceivers in Figure 6. B) Comparison of delayed trigger technique with sampling without delayed trigger.

SYSTEM AND METHOD FOR PHASED ARRAY MATERIAL IMAGING

CROSS-REFERENCE TO RELATED APPLICATIONS

Related Applications

Related applications: This application is a continuation application of application Ser. No. 15/061,116 filed on Mar. 4, 2016, which claims priority to U.S. provisional patent application Ser. No. 62/129,344 filed Mar. 6, 2016, each of which is incorporated herein in their entirety.

A. Field of Invention

A system and method for mapping a material, object or organ (pathology) is presented using improved Transmit/Receive (T/R) imaging techniques and a multiplicity of sensors. The sensors may be ultrasound, acoustic, electromagnetic or other type of sensors.

B. Description of Prior Art

Phased array imaging techniques have been applied to ultrasound, electromagnetic (RADAR), optical and acoustic (SONAR) sensors. Phased array systems are used extensively in non-destructive evaluation, biomedical imaging, underwater imaging and RADAR and others. The prior art techniques use an array or a matrix of waveform transceivers. Individual transceivers are designed to produce a far field pattern. A time delay or a phase shift pattern is introduced between individual transceivers resulting in an interference pattern. The interference pattern effectively steers the transmitted beam in a desired direction or at a focal point.

Figure 1:
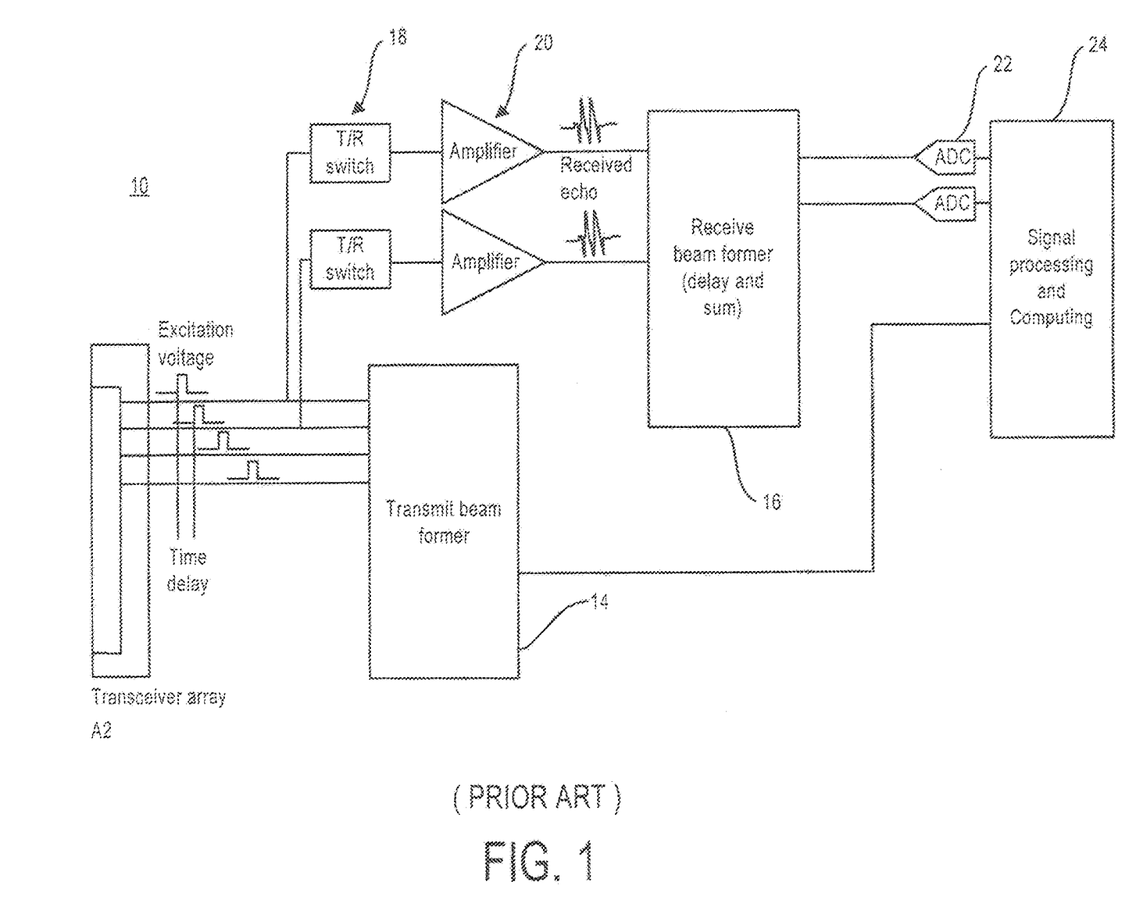
FIG. 1 shows a block diagram of a known system using a phased transceiver array.

As shown in FIG. 1, a conventional phased array imaging system 10 may consist of the following major components:
1) a transceiver array 12;
2) a transmit beam-former 14;
3) a receive beam former 16,
4) SPDT (Single Pole Double Throw) Transmit/receive switches 18 (one for each transceiver of the array 12,
5) Amplifiers 20,
6) Analog to digital converters (ADCs) 22
7) at least one signal processing and computing device 24.

Figure 2:
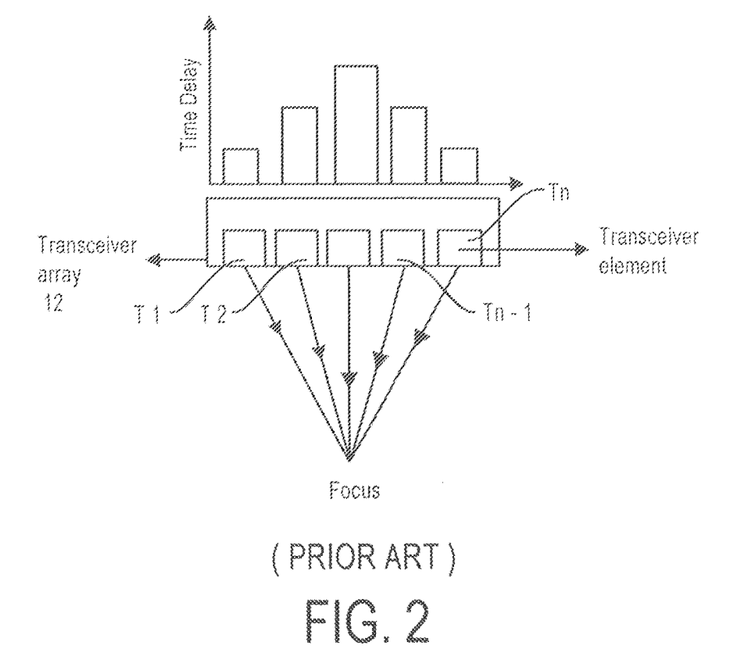
FIG. 2 shows a plurality of beams transmitted from transmitters to single focal point.

The transmit beam former 14 and/or switches 18 excite (turns on/off) the transmitter elements in the transceiver array 12 at precisely timed intervals. In FIG. 2 the transmitter elements T1, T2, . . . Tn-1, Tn of array 12 are shown with transmitters T1 and Tn being the farthest from a focal point or focus F, transmitter elements T2 and Tn-1 being closer to the focal point F, and so on. The transmitter elements T1, Tn are excited (and/or switched on/off) first, transmitter elements closer to the focal point (2, Tn-1 are excited after a predetermined time delay, and so on.

Figure 3:
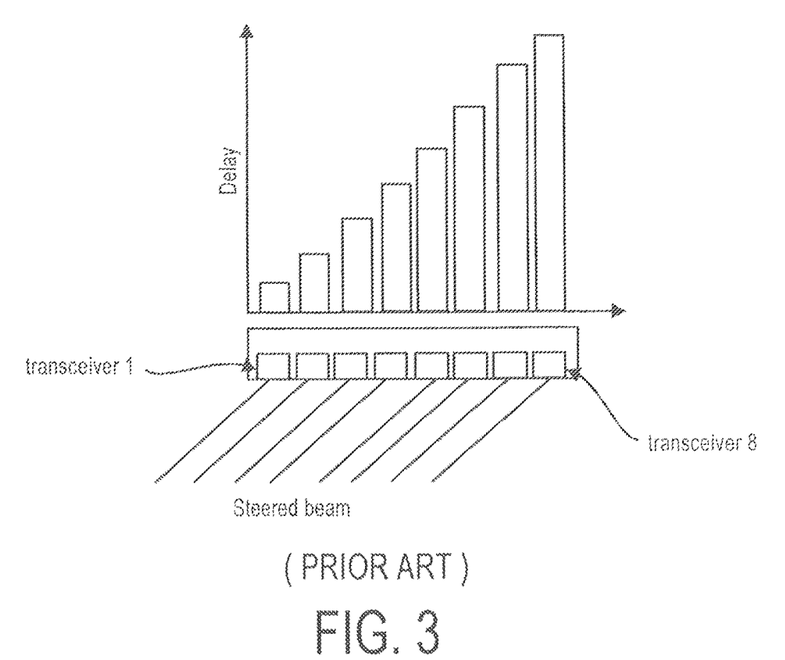
FIG. 3 shows a plurality of parallel beams from transmitters directed at an angle with respect to a surface of an object.

Alternatively, as shown in FIG. 3 directional steering may be used, in which case the transmitter elements T1 . . . T8 are excited by respective excitation wave or pulses that are provided either with time delays or phase shifts or a combination of both time delays and phase shifts. Phase shifts for directional steering of beam are most common in RADAR (electromagnetic) phased arrays. All these excitation signals are produced by the transmit beam former 14.

When the beams from transmitters hit a target, the resulting interference pattern produces echoes from the region under observation. These echoes are detected and collected by individual receiver elements Time delays that are introduced during the excitation phase of the process are taken into account in summing the received waveforms. The receive beam former 16 performs the task of delaying the received waveforms and summing them.

Because often the received waveforms are highly attenuated, an 'analog front end' amplifiers 20 are needed before the receive beam former 16 can delay and sum the waveforms. Often high voltages are involved during the excitation or transmit mode and hence SPAT transmit-receive switches 18 are required to protect the analog front end amplifiers 20 and the receive beam former 16 from damaging high voltages. Analog to digital converters 22 interface the receive beam former 16 to a signal processing and computing device 24. The computing device 24 also includes a graphic user interface (not shown) and further means (not shown) to present the received echoes in human understandable format.

Due to electronic focusing and beam steering, phased array based ultrasound, SONAR and RADAR systems generate outputs with sharper focus, a variable depth of field and reduced mechanical complexity as compared to prior technology. However, the present state of the art suffers from significant technological and functional drawbacks which result in:
1. High cost of phased array imaging systems
2. Noise due to power supply.
3. Ringing and blind zone distances.
4. Reduced accuracy and resolution of phased array imaging systems.
5. Due to the above and other technological drawbacks, the miniaturization of phased array systems is hindered.

More specifically, the disadvantages of current phased array imaging systems such as the ones illustrated in FIGS. 1-3 include:

1) The requirement for SPDT T/R switches 18: As discussed above, these T/R switches 18 are used to protect the receive amplifiers 20 and the receiver beam former 16 from destructive high excitation transmit pulse voltages. T/R switches have a switching time delay, typically in range of tens of nanoseconds. For the beam former 16 typical delay times are in range of few nanoseconds. Hence, the T/R switches 18 introduce significant electrical and electronic complexities in phased array imaging systems. Additionally, many advanced T/R switches 18 often need a digital programming signal to either enable them or to control bias currents. Due to this requirement for T/R switches, amplifiers are not integrated directly with transceivers. This is especially a problem in ultrasound phased array systems. Since the amplifiers are not physically close to the transceivers, noise and time delays are introduced as the received (very low level) echo signals travel through cables from the transceivers to T/R switches. Further, T/R switches have their own electrical characteristics which convolute (distort) the received echoes with 'noise', thereby introducing further inaccuracy.

2) Large number of ADCs 22: Current phased array systems require analog to digital converters of the order of the number of transceiver elements. This increases the cost and complexity of the current phased array imaging systems.

3) High performance ADCs 22: Current phased array imaging systems require a very precise time delay from the transmit beam former. For example, in a current ultrasound phased array system, a typical time delay could be as small as 1-2.5 ns. Since the received echoes need to be time delayed as well, this would mean an ADC capable of sampling at 1 GHz or faster. Ultrasound signals are typically only 1-50 MHz; hence a much higher speed ADC is required to process the time delay. Therefore, using high performance ADCs drastically increases the cost and complexity of the current phased array systems. It further increases the memory requirement in signal processing by up to 1000 times for phased array ultrasound systems. Additionally, due to the high computing resources required, the imaging frame rate is extremely slow, causing blurry images, and less accurate final imaging.

4) High performance computing and signal processing device 24: Due to the above discussed high cost of high performance ADC's, an alternate to using high performance ADCs is to use 'interpolation filtering' or some other computational technique to sum and delay the received echoes. However, this still requires large memory and computational power, reduces accuracy/resolution as well as increases cost due to the need for high computing resources.

5) Significant electrical noise introduced by the high voltage power supply: Either electromagnetic or ultrasonic, the received voltages in the present state-of-art phased array imaging signals are several orders of magnitude smaller than the transmitter pulsing voltages. In present state-of-art systems, the high voltage components (50-200 volts for ultrasound) are electrically connected to low voltage receiver elements (for ultrasound, received voltages are a few millivolts). This is because both transmitter and receiver elements are not electrically isolated (share a common electrical point (ground)), as illustrated for example in US Patent Application Publication 2010/00274139. Hence even a small noise in high voltage power supply leads to significantly larger noises in analog front end, low noise amplifier etc. The additional noise in the received waveforms/echoes means that—1) additional computational resources or analog electronics has to be dedicated to reduce the noise 2) High pulsing voltages need to be used to excite the transmitter. Both of these have a detrimental effect on image quality, miniaturization, cost as well as health hazard (in case of ultrasound, high pulsing voltages cause tissue heating and damage).

6) Ringing and blind distance: As a result of 1) transmitter and receiver elements not being electrically isolated and 2) the transmitter continuing to vibrate even after the pulsing voltage is removed, near surface object objects cannot be imaged.

SUMMARY OF THE INVENTION

The present invention is concerned with the design of an efficient phased array imaging/material mapping system without T/R switches and with a lesser number of low sampling speed ADCs. The invention further provides for electrical isolation between LNA (Low Noise Amplifiers) and high voltage power supply, different ground electrical reference point, dramatically reduced noise.

The invention also reduces the required memory size and therefore reduces the need for computing resources and costs. The invention includes dedicated transmitters and receivers instead of using the same phased array element (piezoelectric/capacitive/magnetostrictive/antennae etc.) as both the transmitter and the receiver (transceiver).

In one embodiment, a phased array probe is presented that includes a plurality of transmitters and receivers wherein at least one of said transmitter is a reference transmitter and all other transmitters are laterally offset from said reference transmitter, and wherein at least one receiver is a reference receiver with all the other receivers being laterally offset from said reference receiver;

a beam former generating control signals for exciting each said transmitter, a pulse generator generating excitation pulses to said transmitter in response to said control signals, in response said transmitters sending respective probe signals to a target or other object of interest, the excitation pulses to all other transmitters being delayed by a period related to said lateral offset;

a receiving module receiving echo signals from said receivers corresponding to said probe signals, said receiving module delaying echo signals from said all other receivers by delays related to said lateral offset; and an analyzer analyzing said echo signals.

The transmitters are one of piezoelectric, capacitive, magnetostrictive, acoustic, electromagnetic and any other transducer elements converting electrical voltage pulses into acoustic, ultrasonic or electromagnetic waves.

The probe may include low noise amplifiers amplifying signals from said receivers to generate said echo signals. The receiving module may include ADCs converting the echo signals into corresponding digital output signals.

Preferably, echo signals are delayed by respective amounts with said echo signals from all the receivers occurring simultaneously. Once they processed, the echo signals can be summed or added resulting a single well defined, clean signal.

In one embodiment multiplexers may be used to reduce the number of components.

DETAILED DESCRIPTION OF THE INVENTION

Figure 4A:
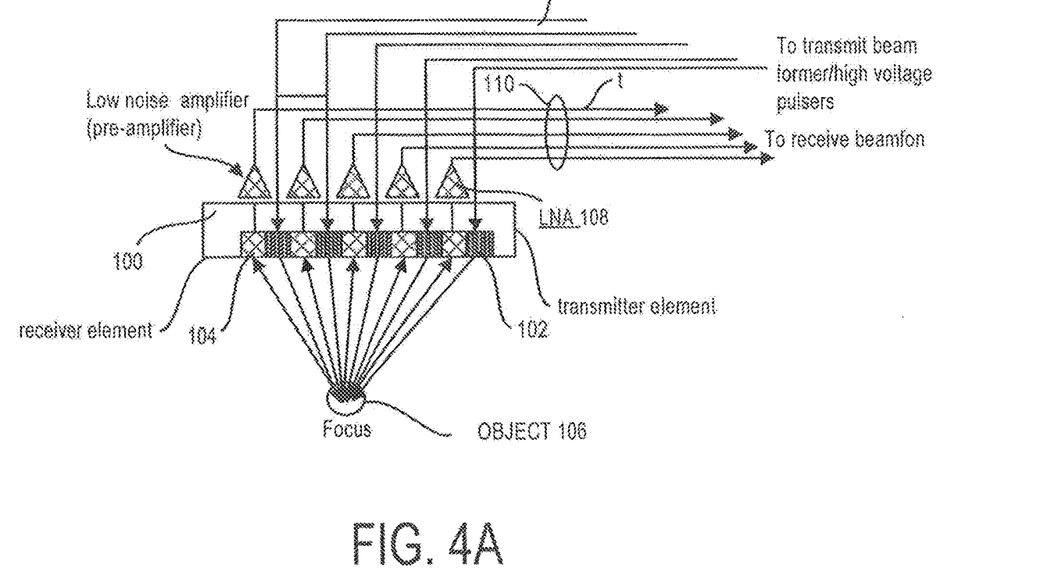
FIGS. 4A and 4B a block diagram and a two-dimensional layout of a sensor array configured in accordance with this invention.
Figure 4B:
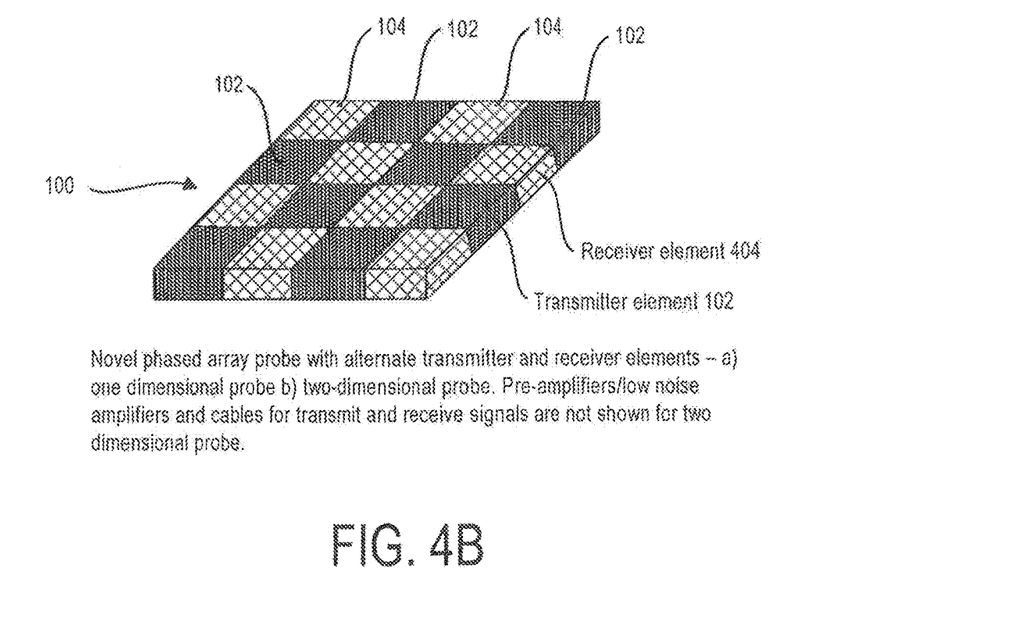

FIGS. 4A and 4B shows a novel configuration of transceiver array 100 with alternate (separate) transmitters 102 and receivers 104. The transmitters 102 are excited by high trigger signals t from a beam forming circuitry (not shown) in this figure. Both transmiters 102 and receivers are aimed a target or object 106. The reflected signals are sensed by receivers 104 and corresponding received signal r (after amplification by amplifiers 108 are sent by a separate set of lines to a signal processor (not shown in this drawings).

As T/R switches used in prior art systems are not required, a low noise amplifier (LNA) and/or preamplifier 108 can be placed physically close to the respective receiver 104, eliminating noise, time delays and possibly fragile cables. The LNA 108 is an analog electronic device that is easily integrated with the phased array 100 using well known solid state integration technology at low cost. Since the received signals r are amplified at a considerably reduced connection distance, the signal to noise ratio improves significantly and little, if any, additional noise is picked up in the cables 110 between the LNA and the receive beam former circuitry due to the higher signal levels. The receive beam former circuitry could be provided on a separate chip disposed near array 100 or could be integrated on the same IC chip. This would also result in a significantly improved accuracy, resolution and lower costs as compared to the prior art.

FIG. 4A shows the novel phased array sensor 100 in a one dimensional near configuration. However similar arrangement is possible in a two dimensional matrix form as well as shown in FIG. 4B. Even though the amplitude of the received signals may be reduced by half, the LNA can have gain in the range of 10-100 so that the resultant signal to noise ratio is still much higher than prior art. This novel phased array sensor shown in FIGS. 4A and 4B may be integrated (and may be substituted in conventional system) with existing phased array instrumentation without any major changes to existing hardware or software.

Figure 5:
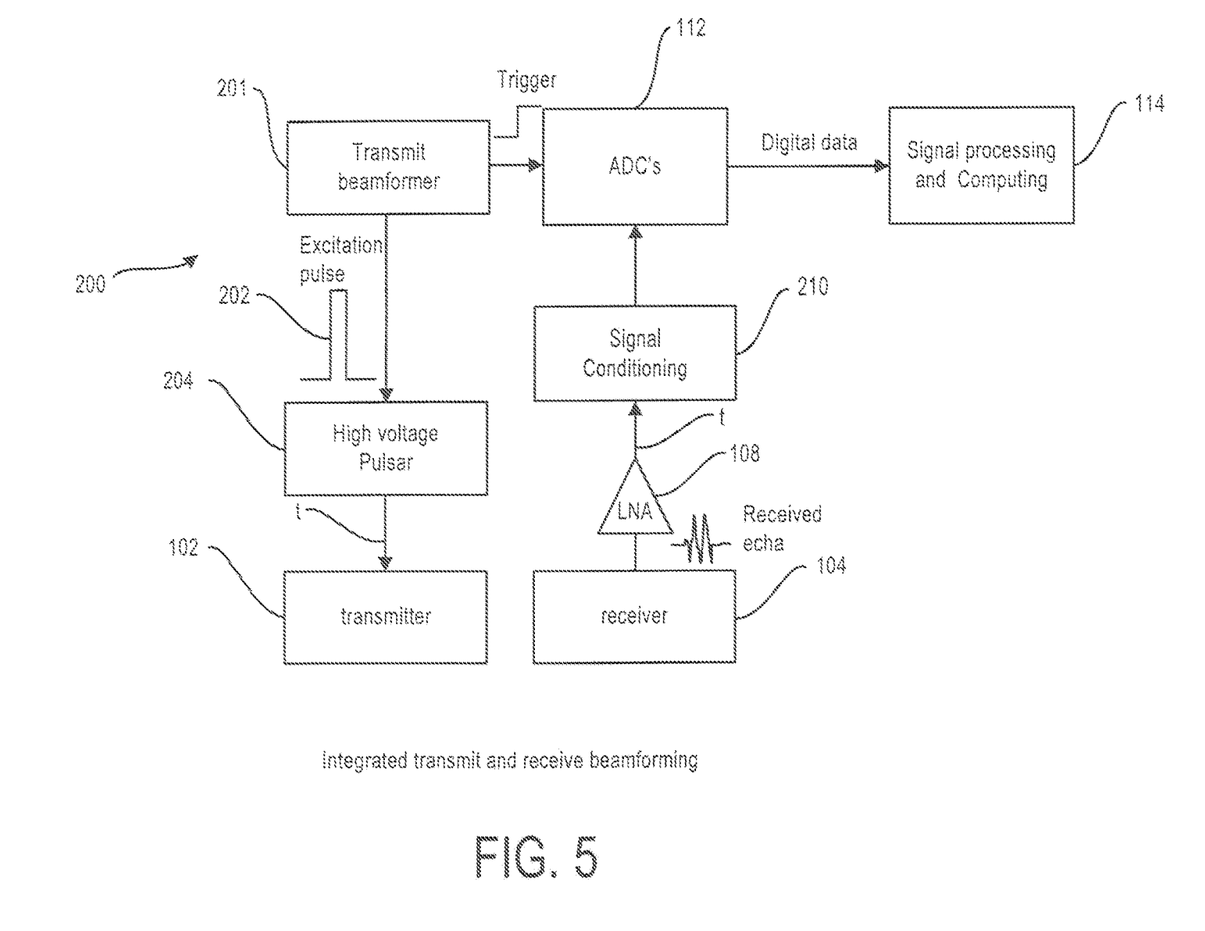
FIG. 5 shows a block diagram of a sensor system using the array of FIG. 4.

However, in the present application a transmit and receive beam former circuit is presented in order to reduce both the number and the sampling frequency of ADCs. In the proposed new circuit shown in FIG. 5, the receive beam former used in conventional systems (such as the one described in the US Patent Publication identified above) is eliminated. In conventional systems, the transmit beam former consists of a type of programmable logic device such as a field programmable gate array (FPGA) or a phase shifter. As shown in FIG. 5, the transmit beam former initiates high voltage excitation pulses, it also generates appropriately delayed 'trigger' pulses for ADC digitizer "programming" in such a way that the received echoes (or received signals) are aligned properly so as to increase resolution. This further serves to increase system accuracy and reduce costs.

More specifically, referring to FIG. 5, the complete system 200 includes a transmit beam former 201 that generates control signals to a high voltage pulser 202. In response, the pulser 202 generates high voltage excitation pulses (of an appropriate magnitude and duration) to each of the transmitters 102. In response, the transmitters 102 generate a signal to the target or object of interest 106. The signals reflected from the target 106 (or echoes) are sensed by receivers 104. The received signal from each receiver is amplified by amplifier 108, conditioned (e.g., filtered, etc., by a signal conditioner 210 and provided to a bank of ADC (analog to digital converters) 212. The beam former 201 also sends a set of trigger or delay signals to the ADC bank 212 to delay all or some of the received signals. The ADCs start sampling the received signals only after they receive their respective trigger. These signals are therefore appropriately delayed and hence can be summed (or a weighted average operation can be performed) by the signal processing and computing module 214.

Figure 6A:
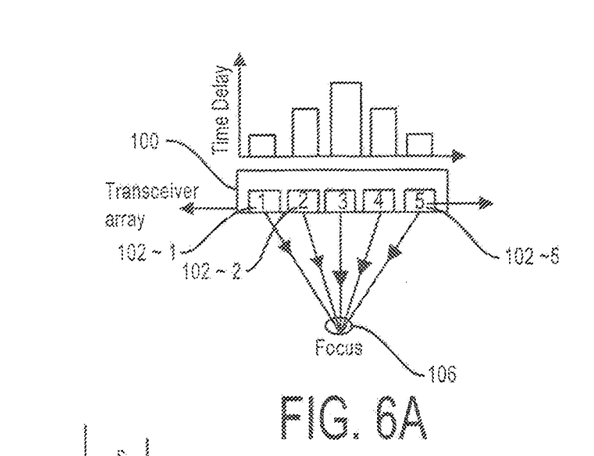
FIGS. 6A, 6B, 6C and 6D show respectively the sequence of responses from a group of linear receivers in accordance with this invention, the sequence of excitation pulses sent to the linear receivers, the timing of the received waveforms from the receivers, and the sequence of delays applied each trigger signal to achieve shapeforming.
Figure 6B:
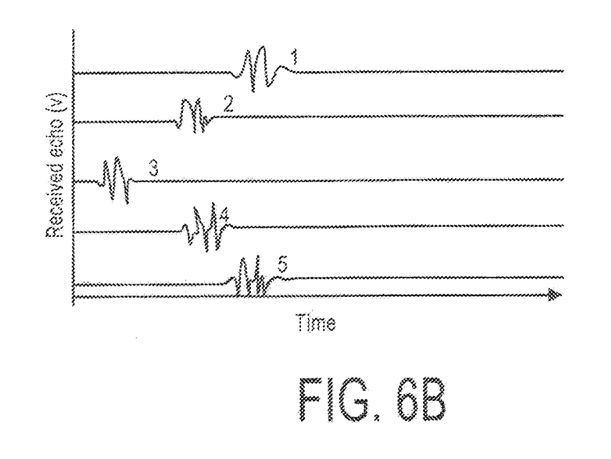

FIGS. 6A-D illustrates the use of delay signals to align received echoes. For simplicity, let us assume a five element phased array 100 (with equally spaced transmit elements 102-1, 102-2 . . . 102-5) is used to focus on target 106 disposed at a focal point which lies on the perpendicular bisector of the phased array. Since transmitter 102-1 and 102-5 are farthest from the focal point, they are excited first. Transmitter 102-3 is excited after a time delay σ from transmitters 102-1 and 102-5. Transmitter 102-2 and 102-4 are excited after a time delay of σ from transmitter 102-3 as shown in FIG. 6B.

Figure 6C:
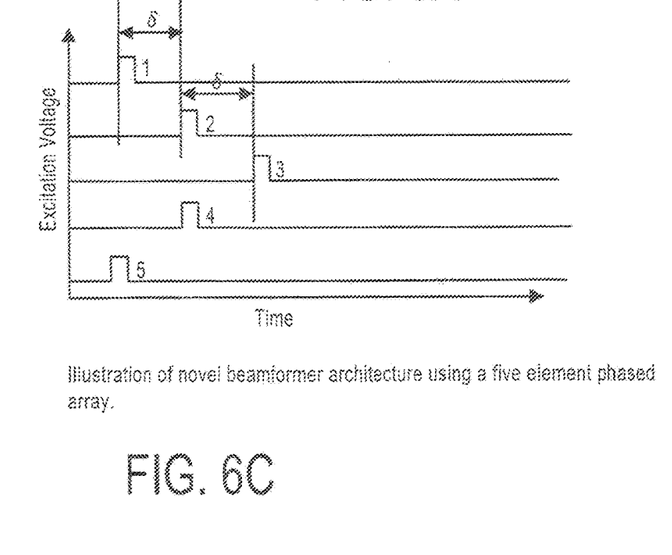
Figure 6D:
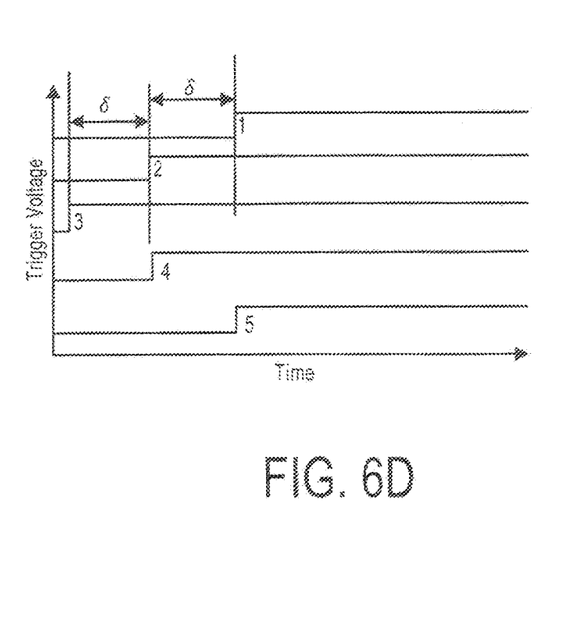

This results in all the waveforms/pulses interfering constructively at the focus. The resultant echoes from the focus arrive at the respective receivers (which have been omitted from FIG. 6A for the sake of clarity) at different times as shown in FIG. 6C with the echoes from the receiver associated with transmitter 102-3 arriving at the earliest. To sample the received echoes, we can use trigger signals as shown in FIG. 6D, so as to compensate for the time difference due to the path difference for different transceiver elements.

Figure 7A:
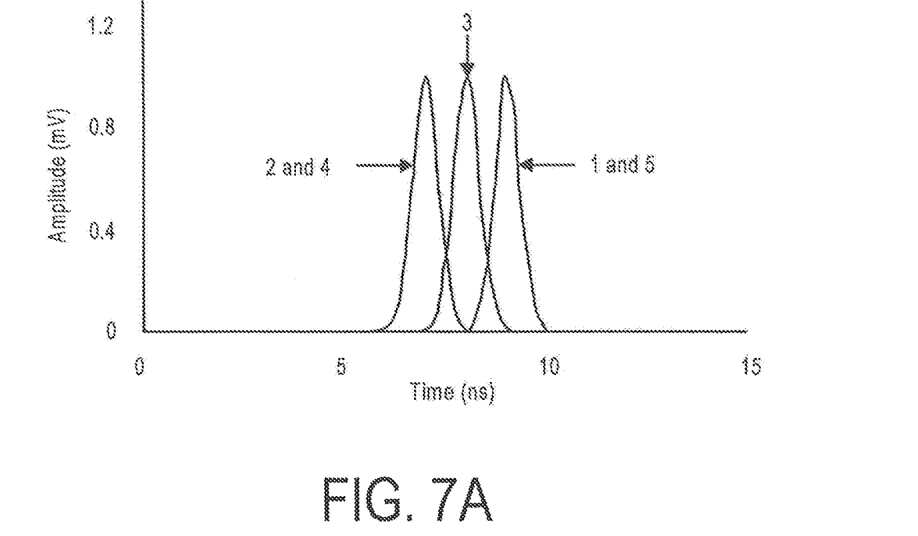
FIG. 7A shows the waveshapes from the linear receivers with no delay.
Figure 7B:
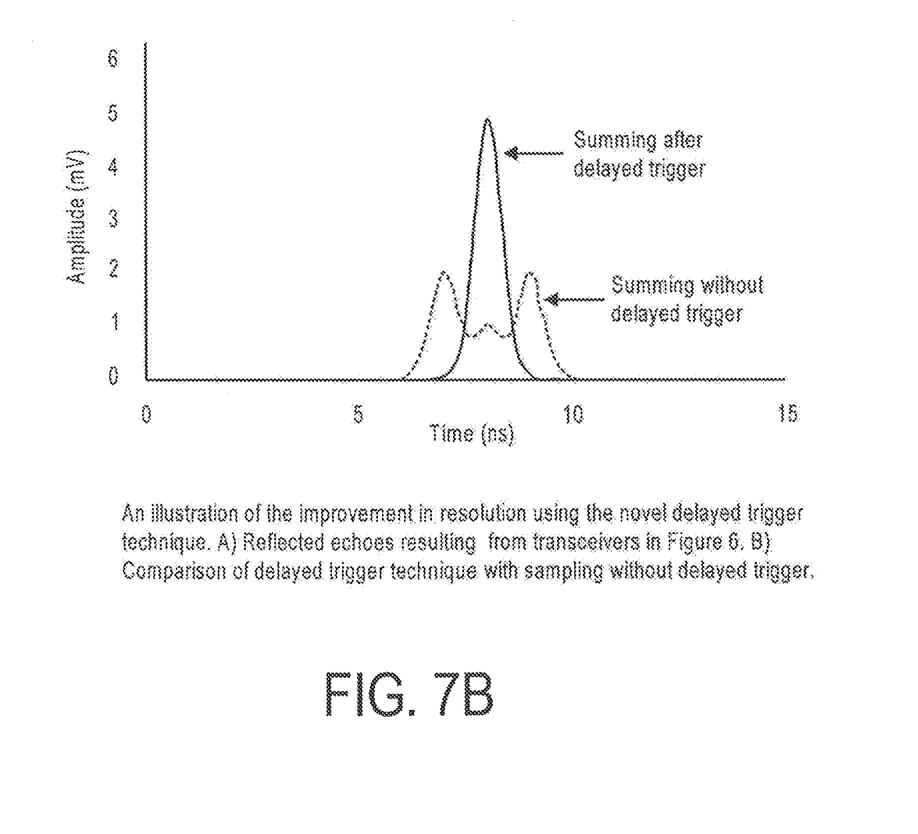
FIG. 7B shows the wave shapes of the linear receivers with the delays shown in FIG. 6D.

FIGS. 7A and 7B show the echo pulses from transceivers and the effect of sampling using our novel technique (delayed trigger) versus sampling without using delayed triggers (current state of art). Notice that there is a marked improvement in accuracy. As described in section B (prior art), an alternate to using the delayed triggers is to use either high sampling frequency ADCs or to use interpolation filtering. Both these techniques used in present art result in either high cost, reduced resolution or both.

The illustration in FIGS. 7A and B show the improvement in resolution/accuracy just for 5 element phased array. FIG. 7A shows five signals received from the five receivers. Obviously it is difficult to analyze these signals to get information about the target 106. FIG. 7B shows the combined with and without the delays. Obviously delaying and summing the signals results in a combined signal that is much easier to analyze.

However, in practice, the number of transceiver elements in the phased array can be in several hundreds and hence the resolution/accuracy without delayed trigger will be very poor as the number of transceiver elements increases.

The digital data from all the receivers is already offset by a suitable delay originating from the transmit beam former and hence can be added as such without any interpolation. Hence, for a 10 MHz ultrasound signal with 1 ns delay, an ADC/Digitizer with 10 MHz sampling frequency can be used instead of possibly a 1 GHz sampling ADC. Hence, less computing resources are required to process the received ultrasound echo signal.

Figure 8:
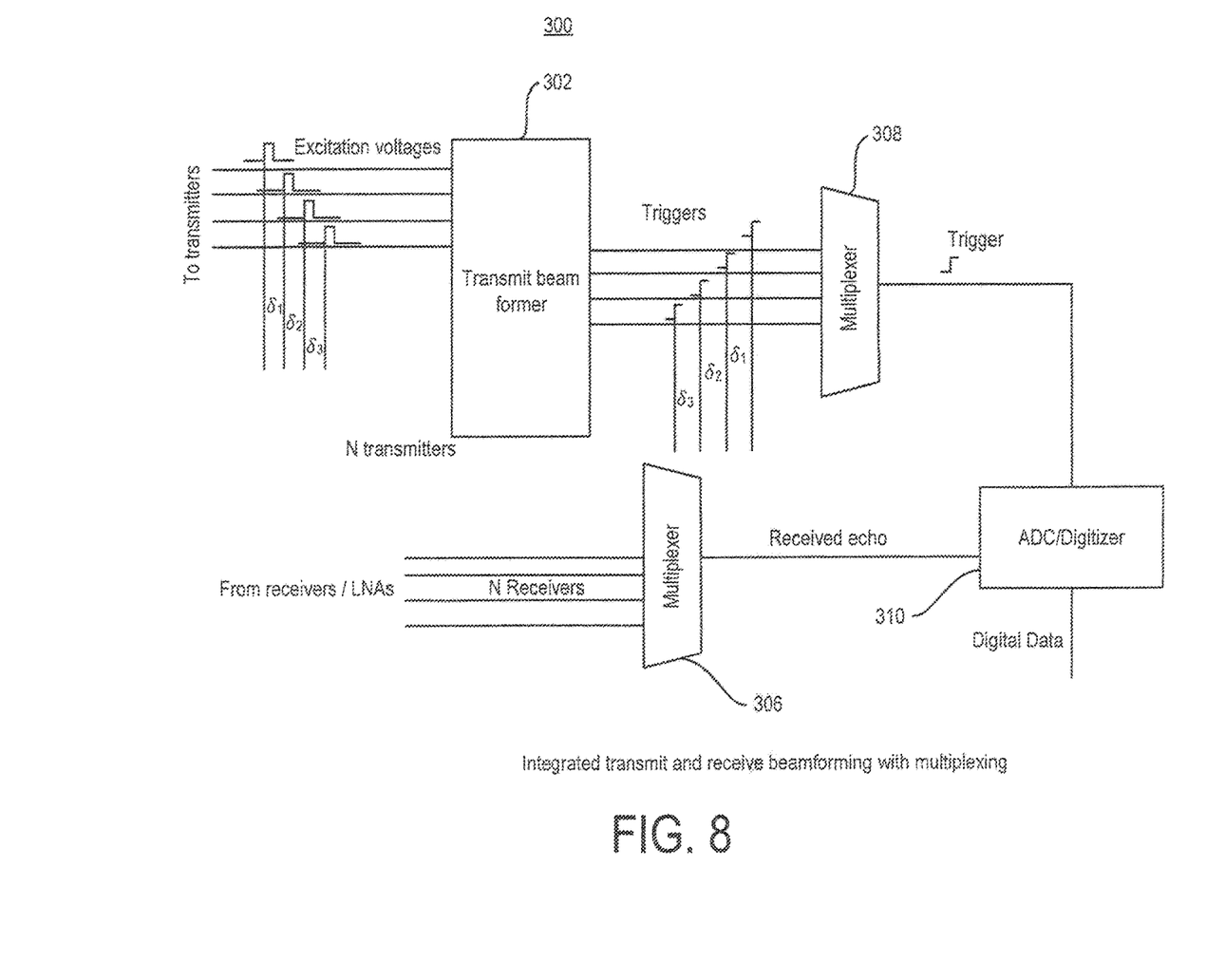
FIG. 8 shows a block diagram of a sensor system constructed in accordance with this invention using multiplexers.
Figure 9:
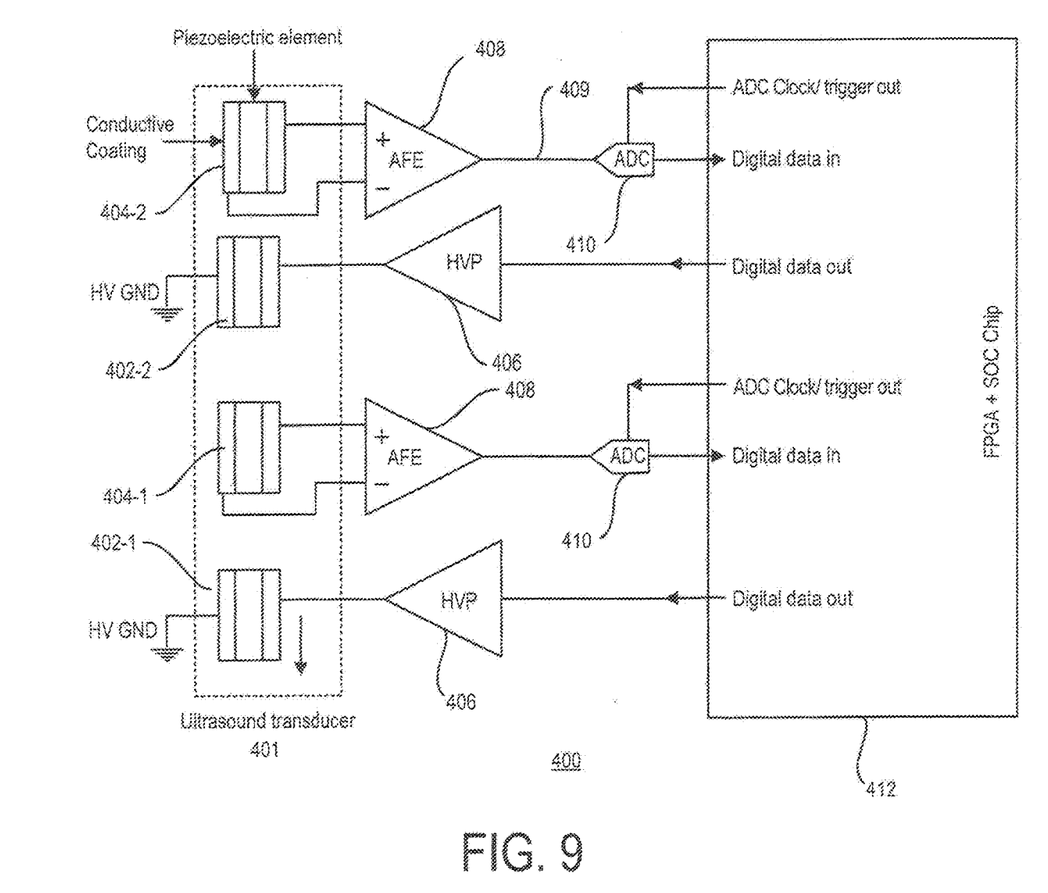
FIG. 9 shows a block diagram for a real time, small size, high resolution ultrasound imaging system for biomedical or industrial imaging constructed in accordance with this invention.

Further, a multiplexer can be used to reduce the number of ADCs as well, further reducing the cost. AnN:1 multiplexing architecture 300 (with N being the number of receivers) is shown in FIG. 8. During the transmit stage, all the transmitters are excited by the transmit beam former 302. However, during the receive stage, both the trigger signals as well as received echoes from the receivers are multiplexed using two multiplexers 306, 308. Only one received echo goes to the analog front end and ADC/Digitizer at a time and the corresponding trigger signal switches on the ADC/digitizer. Once an echo is digitized, it is stored in the computer memory and the next echo is digitized, keeping the delay law pattern in the transmit beam former identical. Since all the echoes are appropriately offset and properly 'referenced', all the echoes can be added up within the ADC/digitizer 310 after all the receiver data have been acquired.

Alternately, the digitized echoes can be added up sequentially as they are acquired. Even though FIG. 8 shows N:1 multiplexing architecture however N:K multiplexing scheme can be adopted as well, where K is the number of analog-front end and ADC/digitizer pairs. The N:K multiplexing will be higher frame rate than N:1 multiplexing but the cost will be higher than N:1 multiplexing. By a suitable selection of N and K, the cost and frame-rate can both be optimized. The novel integrated beamforming architecture with or without multiplexing can be used either with existing phased array probes or with the novel phased array probes without T/R switches or with novel phased array probes with electrical isolation between transmitters and receivers.

The electrical isolation between transmitter and receiver elements will completely eradicate the noise from high voltage component of the system to cross over to the low noise amplifiers. In addition, blind distances will be completely eliminated through the electrical isolation of transmitters and receivers. This will enable the imaging of near surface artifacts as well as possible reduction in transmitter pulsing voltages.

Reduced voltages also will provide for safer "in body" medical imaging, meeting newer food and drug administration (FDA) restrictions on high voltage in medical examinations.

The multiplexed architecture is especially suitable for materials testing applications where the test specimen is 'static' or changes very slowly. For example, using the multiplexed architecture, a low cost real-time ultrasonic monitoring system for civil or energy infrastructure such as oil/gas pipelines can be designed and permanently fixed to the structure.

Figure 10:
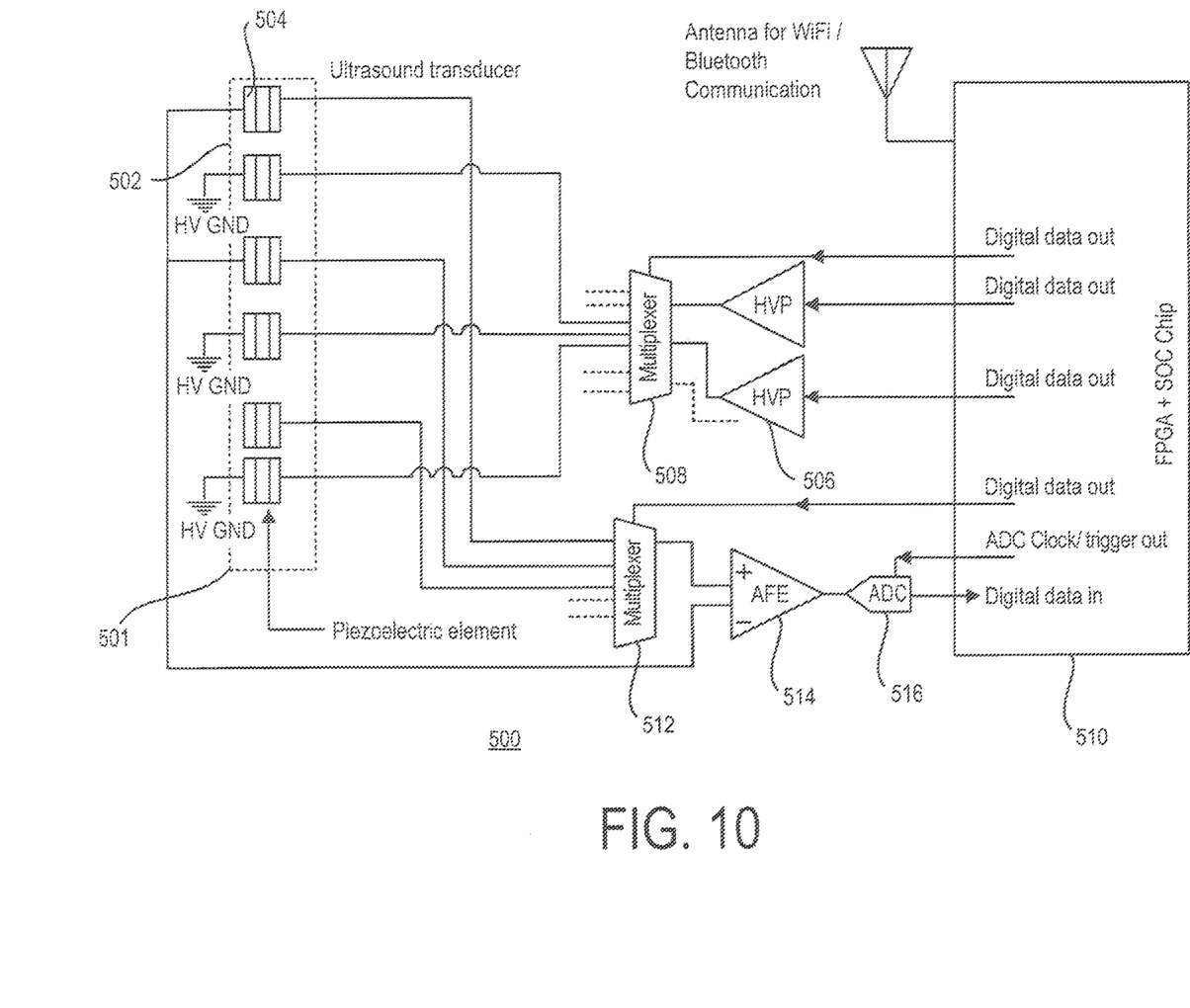
FIG. 10 shows a block diagram of a high resolution, low cost ultrasound system for structural condition monitoring constructed in accordance with this invention.

A 1-20 MHz high resolution and small sized phased array ultrasound system 400 constructed in accordance with this invention is now described in accordance with this invention in conjunction with FIG. 10. The transducer 401 consists of a number of alternate transmitter 402-1 . . . and receiver elements 404-1, . . . (only two each shown in Figure). The receiver elements 404-1, . . . are connected to an analog front end (AFE 408) chip such as MAX 2077 (Maxim Integrated) for amplification. The transmitter elements 402-1 . . . isolate the receivers from high voltage circuitry, effectively reducing noise in received ultrasound signals. The AFE 408 includes a number of low noise amplifiers, time gain amplifiers and low pass (anti-aliasing) filters. The transmitter elements 402-1, . . . are connected to a high voltage pulser (HVP) 406 chip such as STHV748 (ST Microelectronics) or MAX4940 (Maxim Integrated). The HVP chip 406 produces an up-to 200 volt peak-peak pulse. The AFE output 409 is connected to a high speed ADC 410 such as AD-9248 (Analog Devices). A 200MSPS ADC will be sufficient for frequencies in range of 1-20 MHz. The ADC clocks obtained from am FPGA 412 are appropriately delayed (in steps of 1 ns) to enable receive beamforming. ADC clocks as well as the digital data to configure both HVP and AFE are generated by the FPGA 410 such a FPGA-SOC chip such as Altera Cyclone V SoC. The FPGA-SoC also collects the digital output from ADC to form a human readable ultrasonic image.

A high resolution and extremely low cost ultrasound system 500 for structural condition monitoring applications is shown in FIG. 11.

In certain applications (mainly industrial) such as monitoring of wind turbine blades, oil and gas pipelines and aerospace structures, it will be very useful to have a low cost sensor system permanently attached to the structure which can monitor the structure. In such structural condition monitoring applications, instantaneous imaging is not necessary. However, the imaging resolution (typically micrometers) cannot be sacrificed. At the same time, cost saving becomes critical. Using the present invention, create a high resolution yet low cost system can be created. The system saves cost by reducing the number of ADCs significantly.

As an example, for an oil pipeline of the diameter of 32 inches, an ultrasound transducer (typically 1-5 MHz) of several hundred thousand elements will be required to cover the entire circumference of the pipeline over the cylindrical length of, say, 6 inches. For such an application, reduction in the sampling frequency and number of ADCs is the key to reducing the system cost. As discussed in previous sections, for a 5 MHz phased array transducer, our novel design enables the transmit beamforming with an accuracy of 1 ns while using ADCs in the range of 50-100 MSPS. This design has enormous cost savings as compared to using ADCs in 1 GHz MSPS for a 1 ns delay. Secondly, we reduce the number of ADCs by using an analog multiplexer after the receiver elements. Since the data from each ADC is precisely timed, the ADC digital output can be stored in FPGA-SoC memory and can be summed/processed at a later time. In addition to reducing the number of ADCs, we can also reduce the number of AFEs successfully. Similarly, the number of HVPs can be reduced by using a high voltage high speed analog switch such as MAX 4968 (Maxim Integrated). Alternately, HVPs can be replaced by high voltage field effect transistors (FETs) and the FETs can be integrated permanently with the ultrasound transducer. This will reduce the amount of noise and jitter during transmit beam forming improving resolution and accuracy.

The digital data acquired from ADCs can be communicated to another computer through a WiFi/Bluetooth or other suitable topology. Ultrasonic measurements in a given area can be compared over time. This can enable detection of subtle changes in the structure such as hydrogen cracking (for oil and gas pipelines) or matrix micro cracking (in fiber composite structures such as wind turbine blades or carbon fiber aircraft structures). Small changes such as these go undetected in normal ultrasonic measurements due to high background noise. Automated monitoring of such small changes using permanently mounted phased array ultrasonic sensors can enable early warning about catastrophic failure and can increase the service lifetime of structures.

The system 500 includes a sensor array 501 including transmitters 502 and receivers 504. High voltage pulses are generated by pullers 506 and fed through multiplexers 508 to the transmitters 502. The echoes or received signals from the receivers 504 are multiplexed by multiplexer 512, amplified and conditioned by AFE's 514, digitized by ADC's 516 and then fed to the FPGA 510 for analyses. As before clock signals for the ADCs 516 and pulsers 506 with suitable delays are generated by the FPGA 510.

Present phased array ultrasound systems are extremely expensive and so are almost operated by skilled technicians and not affixed to the structure for automated monitoring. However, as the novel architecture embedded in equipment is expected to reduce the costs drastically, the phased array ultrasound device can be fixed to the monitored infrastructure at a particular spot. Alternately, 'smart pipelines' can be fabricated with built-in phase array transducers.

Numerous modifications may be made to the invention without departing from its scope as defined in the appended claims.

We claim:

1. A phased array probe, comprising:
   a solid state array including a first transmitter, a second transmitter, a first receiver and a second receiver, each of the first transmitter, second transmitter, first receiver and second receiver being distinct and respectively coupled to distinct signal paths;
   first and second amplifiers integrated with the solid state array and respectively coupled to the first and second receivers;
   a transmit beam former configured to
      generate control signals to respectively excite the first and second transmitters, a control signal associated with the second transmitter being delayed with respect to a control signal associated with the first transmitter, and
      generate a trigger signal corresponding to the delay;
   a pulser generator configured to generate excitation pulses to the transmitters in response to the control signals thereby causing a probe signal transmitted by the second transmitter to be delayed with respect to a probe signal transmitted by the first transmitter;
   a receiving module configured to
      receive signals from the first and second amplifiers corresponding to the probe signals, and
      delay sampling of the received signal associated with the second receiver based on the trigger signal generated by the transmit beam former; and
   an analyzer configured to analyze the received signals.

2. The probe of claim 1, wherein the receiving module includes at least one analog-to-digital converter that converts the received signals into digital output signals.

3. The probe of claim 2, wherein the trigger signal of the transmit beam former is coupled to the analog-to-digital converter to respectively delay sampling of the received signals.

4. The probe of claim 2, further comprising a memory configured to store digital values output by the analog-to-digital converter.

5. The probe of claim 4, wherein the receiving module is configured to perform a summation of the stored digital values.

6. The probe of claim 1, wherein the delayed received signal associated with the second receiver overlaps with the received signal associated with the first receiver.

7. The probe of claim 1, wherein the first transmitter and the second transmitter are coupled to a high voltage ground.

8. The probe of claim 7, wherein the first receiver and the second receiver are coupled to a low voltage reference.

9. The probe of claim 1, wherein the first transmitter includes a transmitter element selected from the group consisting of piezoelectric, capacitive, magnetostrictive, acoustic, and electromagnetic element that converts electrical voltage pulses into acoustic, ultrasonic or electromagnetic waves.

10. The probe of claim 1, further comprising a multiplexer that multiplexes a plurality of trigger signals generated by the transmit beam former, and the transmit beam former provides a multiplexed trigger signal to an analog-to-digital converter.

11. The probe of claim 1, wherein the receiving module includes a multiplexor that multiplexes the received signals and provides the multiplexed received signal to an analog-to-digital converter.

12. A method of probing a target with a probe including a solid state array including a first transmitter, a second transmitter, a first receiver and a second receiver, each of the first transmitter, second transmitter, first receiver and second receiver being distinct and respectively coupled to distinct signal paths, the method comprising:
    generating, by a transmit beam former, a first transmit signal and a second transmit signal, the first transmit signal being delayed with respect to the second transmit signal, the first transmit signal and the second transmit signal being respectively provided to the first and second transmitters;
    detecting a first echo signal with the first receiver and a second echo signal with the second receiver;
    amplifying, respectively using first and second low noise amplifiers integrated with the solid state array, the first and second echo signals;
    delaying, by a receiving module and based on a trigger signal generated by the transmit beam former, sampling the first amplified echo signal relative to the second amplified echo signal;
    converting the first and second echo signals into digital signals based on the sampling; and
    summing the digital signals.

13. The method of claim 12, further comprising sending excitation signals to the transmitters by the transmit beam former to cause the generation of the transmit signals.

14. The method of claim 12, further comprising multiplexing the first and second amplified echo signals.

15. The method of claim 14, wherein the sampling is performed by an analog-to-digital converter, and a trigger signal of the transmit beam former is coupled to the analog-to-digital converter to respectively delay sampling of the received signals.

16. The method of claim 12, wherein the first transmitter and the second transmitter are coupled to a high voltage ground.

17. The method of claim 16, wherein the first receiver and the second receiver are coupled to a low voltage reference.

18. The method of claim 12, further comprising multiplexing a plurality of trigger signals generated by the transmit beam former, and providing, by the transmit beam former, a multiplexed trigger signal to an analog-to-digital converter.

19. The method of claim 12, further comprising multiplexing, by the receiving module, the first and second amplified echo signals providing the multiplexed received signal to an analog-to-digital converter.

* * * * *